(12) United States Patent
Kelly

(10) Patent No.: US 6,558,550 B1
(45) Date of Patent: May 6, 2003

(54) PROCESS FOR TREATING SEPTAGE

(76) Inventor: Robert J. Kelly, 15 Chilton Rd., Brockton, MA (US) 02301

( * ) Notice: Subject to any disclaimer, the term of this patent is extended or adjusted under 35 U.S.C. 154(b) by 0 days.

(21) Appl. No.: 10/134,077

(22) Filed: Apr. 26, 2002

(51) Int. Cl.⁷ .................................................. C02F 3/32
(52) U.S. Cl. ........................ 210/609; 210/615; 210/754; 210/150; 210/175; 210/173
(58) Field of Search .................................. 210/173, 751, 210/601, 609, 631, 743, 615–617, 748, 754–756, 150, 207, 175, 177, 263

(56) References Cited

U.S. PATENT DOCUMENTS

| | | | |
|---|---|---|---|
| 4,554,002 A * | 11/1985 | Nicholson ....................... 71/12 |
| 4,781,842 A | 11/1988 | Nicholson ................... 210/751 |
| 4,829,678 A | 5/1989 | Glorioso ........................ 34/11 |
| 4,852,269 A | 8/1989 | Glorioso ........................ 34/11 |
| 4,902,431 A | 2/1990 | Nicholson et al. .......... 210/751 |
| 4,919,814 A | 4/1990 | Carnahan et al. ............ 210/603 |
| 4,956,926 A | 9/1990 | Glorioso ........................ 34/111 |
| 4,975,195 A | 12/1990 | Urbani ........................ 210/608 |
| 4,989,344 A | 2/1991 | Glorioso ........................ 34/11 |
| 5,013,458 A | 5/1991 | Christy, Sr. et al. ........ 210/751 |
| 5,110,459 A | 5/1992 | Baxter ........................ 210/143 |
| 5,135,664 A | 8/1992 | Burnham ..................... 210/751 |
| 5,186,840 A | 2/1993 | Christy et al. .............. 210/751 |
| 5,229,011 A | 7/1993 | Christy, Sr. et al. ........ 210/751 |
| 5,275,733 A | 1/1994 | Burnham ..................... 210/609 |
| 5,337,496 A | 8/1994 | Glorioso ........................ 34/378 |
| 5,346,616 A | 9/1994 | Christy, Sr. et al. ........ 210/179 |
| 5,401,402 A | 3/1995 | Christy et al. .............. 210/205 |
| 5,405,536 A | 4/1995 | Christy ........................ 210/710 |
| 5,417,861 A | 5/1995 | Burnham ..................... 210/609 |
| 5,433,844 A | 7/1995 | Christy ........................ 210/149 |
| 5,554,279 A | 9/1996 | Christy ........................ 210/149 |
| 5,618,442 A | 4/1997 | Christy ........................ 210/742 |
| 5,681,481 A | 10/1997 | Christy et al. .............. 210/723 |
| 5,744,041 A | 4/1998 | Grove ........................ 210/602 |
| 5,783,073 A | 7/1998 | Christy et al. .............. 210/205 |
| 5,843,507 A | 12/1998 | Harvey et al. .............. 426/482 |
| 5,851,404 A | 12/1998 | Christy et al. .............. 210/723 |
| 5,960,810 A | 10/1999 | Douglas ...................... 137/14 |
| 6,036,918 A | 3/2000 | Kowanko ..................... 422/33 |
| 6,126,827 A | 10/2000 | Johnson, Jr. et al. ....... 210/602 |
| 6,315,903 B1 | 11/2001 | Noyes ........................ 210/601 |

* cited by examiner

Primary Examiner—Chester T. Barry
(74) Attorney, Agent, or Firm—Brown Rudnick Berlack Israels LLP; John C. Serio; Mark S. Leonardo

(57) ABSTRACT

A process and apparatus for the treatment of septage, particularly grease trap waste, is disclosed. The inventive process will convert the septage into Biosolids (sludge) and water dischargeable to the environment. The treated septage achieves pathogen reduction, and reduced vector attraction. Treatment of septage by pasteurization causes the destruction of harmful pathogens. Pasteurization of septage having high water content provides for even temperature elevation and distribution of heat within the thermal mass of the septage allowing for consistent pathogen destruction. An alkaline compound is utilized to form a filter cake from the solids fraction of the pasteurized septage preventing vector attraction, while producing a beneficial bio-solid. The liquid fraction of the septage is treated by biological process allowing for its discharge into the environment.

29 Claims, 5 Drawing Sheets

PROCESS FOR TREATING SEPTAGE

BACKGROUND

1. Technical Field

This invention relates to a process for treating septage whereby septage is defined as liquids, solids, and semi-solid contents of privies, chemical toilets, cesspools, septic tanks, holding tanks, dry pits, grease traps, grit traps, boat pump out stations, or other sewage waste receptacles. More specifically, the invention involves a process for removing pathogens from the septage and for controlling vector attraction while producing bio-solids that can be utilized as a fertilizer or other beneficial use such as soil conditioner. Additionally, the process allows for the removal of the majority of the water component of the septage and provides for its treatment and subsequent discharge into the environment.

2. Background of the Related Art

The proliferation of fast food restaurants and other large scale food processing centers, where food preparation inherently produces fats and grease waste, in conjunction with increasing regulations concerning the disposal of such wastes, have produced a need for an efficient process for its removal and processing in order to control cost and minimize harm to the environment.

Food, grease and oil are present in waste water produced from restaurants and other food processing establishments. This waste water containing fats, grease and oils forms an emulsion that passes through a grease trap, which is required by most local and state regulations, to capture components within the waste water preventing their release into municipal sewer systems or septic systems. Typically, the grease trap comprises an infall pipe, which discharges the water containing grease and food into an underground holding tank capable of retaining large quantities of this unwanted waste. These holding tanks contain barriers that trap and partially separate heavy solids, floating trash and much of the fats, oils and grease produced from food processing and preparation area drains. As a matter of design these grease traps become saturated with solids, trash, fats, oils and grease, and must be drained periodically per local and state health regulations. The draining of these grease traps is accomplished by a tanker truck having a vacuum pump that retrieves the contents of the grease trap for proper disposal.

The discharge of this concentrated wastewater containing solids, trash, fats, oils and grease into a conventional municipal wastewater treatment facility will either deteriorate the efficiency of that municipal facility or cause serve operational difficulties within the municipal wastewater system. In light of these difficulties, there is a reluctance of municipally owned wastewater treatment plants to accept septage and more particularly grease-trap wastes.

The evolution of greater regulatory requirements as to the disposal of these wastes has contributed to escalating costs associated with their proper disposal. Historically, this septage was disposed of by dumping or landfilling the waste after the removal of some of its aqueous components. Unfortunately, untreated septage, both in solid and liquid form, may contain any number of substances toxic to humans and the environment, including, solvents, organic and inorganic compounds and pathogens. The treatment of septage to destroy these pathogens and noxious compounds before placement within a landfill has become increasingly more important due to environmental concerns. Greater interests in the environmental impact of the disposal of septage and the resulting increase in regulatory requirements have caused escalating costs associated with the proper disposal of septage.

Different methods of treating septage have been implemented with varying degrees of success. One prior art method was to dump the septage into an open pit, where it was then mixed with ash and dirt forming a substantially dry material. This resulting dry material was then placed within a landfill. However, this method required valuable and costly landfill space and also had significant odor problems. Additionally, this virtually unprocessed method of treating septage has certain environmental concerns along with vector attraction.

Many newer approaches to septage treatment utilize labor, energy, intensive chemical and biological systems in order to process the septage so that it is suitable for discharge within the environment. Unfortunately, such processes are costly due to the cost of labor, energy and the expense associated with biological and chemical processes. Moreover, these processes often produce materials that are large in volume and have no practical use. Additionally, these chemical and biological treatments of septage can still have detrimental effects on the environment.

One of these methods utilizing chemical and biological treatment uses surfactants to break down fat globules contained within grease trap waste. Once the fats are broken down, microbes are used to ingest the fat particles. Unfortunately, this process is extremely cost prohibitive and labor intensive and has been met with limited success. Additionally, this method also suffers from significant odor problems and vector attraction. Most importantly, this method still requires a significant volume of landfill space.

Another method involves the heating of the waste to remove by skimming the fats contained within such waste. The solids within the waste are removed and the subsequent liquid waste is heated again to remove remaining pathogens. Unfortunately, this process is both labor intensive and costly from an energy standpoint due to the multiple heating of the waste product. Additionally, the removal of solids within such process produces a product that has no known use and is subsequently disposed within costly landfill sites. Furthermore, the solids produced from this process have not been treated for pathogens or vector attraction.

Several recent approaches have been developed to treat the sludge generated at municipal wastewater treatment plants. These processes treat the sludge with a selected alkaline additive such as lime. One method uses the exothermic reaction between the alkaline additive and the water contained in sludge to produce sufficient heat within the sludge to destroy existing pathogens. Another method uses less lime for the exothermic reaction but supplies supplemental heat to the sludge by electrical elements to attain the temperature required to destroy existing pathogens. Both processes use the elevated pH of the sludge caused by the lime addition to reduced vector attraction. Unfortunately, the energy and chemical. costs associated with these processes are extremely high. More importantly, the heating of sludge, a solid material, by the use of electrical elements or excess lime addition does not necessarily produce uniform heating throughout the sludge and subsequently contributes to pathogen reduction that is not predictable.

As a result of the deficiencies of prior art treatment methods in addressing landfill usage, energy costs and detrimental effects on the environmental, there is a need to provide a septage treatment process that has a low, if not beneficial, impact on the environment while being cost effective.

SUMMARY

The present invention is a waste processing facility specifically designed to process septage. Septage is the liquid, solid, and semi-solid contents of privies, chemical toilets, cesspools, septic tanks, holding tanks, dry pits, grit traps, boat pump out stations, grease traps or other sewage waste receptacles. The physical characteristics of septage vary widely. Septage has a percent solids concentration of generally 0 to 10% by volume. The processing facility is designed to handle approximately 100,000 gallons per day of septage during a 12-hour shift, although other varying amounts are contemplated herein. The inventive process will convert the septage to approximately 40 tons of Biosolids (sludge) having a composition of approximately 60% water. The inventive process addresses the following two considerations in the treatment of septage: pathogen reduction (e.g., helminthes (intestinal worms), bacteria, protozoa, and viruses, etc.), and vector attraction (e.g., rodents, birds, insects, and other organisms that can transport pathogens).

According to the inventive method, the septage is treated upon arrival at the processing facility by screening and grinding the raw septage. After the initial treatment, the septage is stored within a receiving tank prior to being transferred to a pasteurization tank. The septage is transferred, in batches, to pasteurization tanks and is pasteurized by the introduction of steam into the tanks thereby elevating the temperature of the septage to 70 degrees Celsius (158 degrees Fahrenheit) or higher for a minimum of 30 continuous minutes. Due to the more efficient thermal conductivity of water compared to solids, heating the septage, with its much higher water content, is more effective at maintaining even temperatures throughout the mass of material than prior art methods which heat processed sludge. Thus, heating (i.e., pasteurizing) the liquid septage as opposed to the higher solids content sludge allows for a more uniform and thorough heat treatment and ensures greater pathogen reduction. Due to the ease of handling a liquid versus a solid and the use of direct heating versus indirect heating, the cost of pasteurization is much lower.

After pasteurization, the septage is transferred to cooling tanks. The cooled pasteurized septage is then transferred to filter press feed tanks where it is treated with an alkali substance such as lime. Sufficient alkali, i.e., lime, is added to the septage to raise the pH to at least 12 and without the addition of more alkali maintain a pH in the filter cake (i.e., sludge) of at least 12 for two hours and a pH of 11.5 for an additional 22 hours. The current federal regulations related to reducing vector attraction requires that the pH of the sludge be maintained at least 12 for two hours without the addition of more alkali and thereafter that it be maintained at a pH of 11.5 for an additional 22 hours without the addition of more alkali. It is contemplated herein that other pH levels and time parameters may be used.

The process of adding an alkali such as lime also binds up the grease and other difficult to dewater materials in the septage. The added alkali acts as a filter aid and allows the septage to be more easily dewatered into a good filter cake. The resulting lime conditioned septage slurry is pumped through filter presses. The filter presses separate the solids from the liquid. The lime that has been added during the process is mostly non-soluble and is retained within the sludge.

The sludge which is dropped from the filter presses has undergone treatment and meets federal and state standards for beneficial reuse as a Biosolid. The Biosolids can be sold or given away to provide nutrients to growing vegetation or to improve the quality of soil for the purpose of growing vegetation.

The liquid that passes through the filter presses flows into an equalization tank that acts as a surge tank. The liquid is then pumped into a neutralization/precipitation tank. Due to the alkali addition, this liquid has a very high pH. In order to neutralize the liquid prior to the biological treatment processes, carbon dioxide is dissolved into the liquid to form carbonic acid. The dissolution of carbon dioxide and the resulting formation of carbonic acid and other species (e.g., bicarbonate and carbonate) lowers the pH. If lime is used as the alkali, calcium carbonate (limestone) precipitates out of solution as the pH of the liquid is lowered. The calcium carbonate drops to the bottom of the neutralizing tank and is pumped to the filter press feed tanks to be removed by the filter presses and added to the sludge.

Once the calcium carbonate is removed, the remaining liquid flows into equalization tanks. The liquid within these equalization tanks has a pH of between 7 and 8.5. The liquid is then pumped into tanks for biological treatment which includes both aerobic and anoxic processes. In the first of the aerobic processes, aerobic organisms consume the carbon (organic material) contained within the liquid thereby reducing its Biological Oxygen Demand ("BOD"). BOD is a measure of the amount of oxygen that is used by the organisms while consuming the carbon. The second aerobic biological treatment process converts ammonia nitrogen ($NH_3$—N) into nitrate nitrogen ($NO_3$—N). In the anoxic process, anaerobic organisms convert the nitrate nitrogen into nitrogen gas that is dissipated into the atmosphere. The water that remains after the biological treatment steps is pumped into clarifiers. In the clarifiers, biomass which sloughs off the biological processes is removed from the water. The clarified water is then pumped through a sand filter to remove suspended solids from the water. The filtered water is then disinfected by the use of Ultra Violet (UV) filtration which kills any potentially live organisms which may have passed through the clarifiers and sand filter. The disinfected water is then discharged to the groundwater, surface water or to a sewer.

Features of the invention include but are not limited to the following: the inventive method pasteurizes septage as opposed to the pasteurization of sludge which is known in the industry and the inventive method creates a usable material (BioSolid) from septage.

BRIEF DESCRIPTION OF THE DRAWINGS

The foregoing and other features and advantages of the present invention will be more fully understood from the following detailed description of illustrative embodiments, taken in conjunction with the accompanying drawings in which.

DETAILED DESCRIPTION

The present invention particularly deals with the processing of grease trap waste that is collected by vacuum trucks from the grease traps of commercial establishments. Typically, raw grease trap waste includes mixed inorganic and organic solids such as bones, paper, plastics, metal utensils, garbage and other waste materials. The remaining components of the traps' waste are fats, oils, grease, surfactants and aqueous components. The trap waste mixture is not readily separable into components which can be readily disposed within municipal sewage systems or within landfill areas.

Figure 1A:
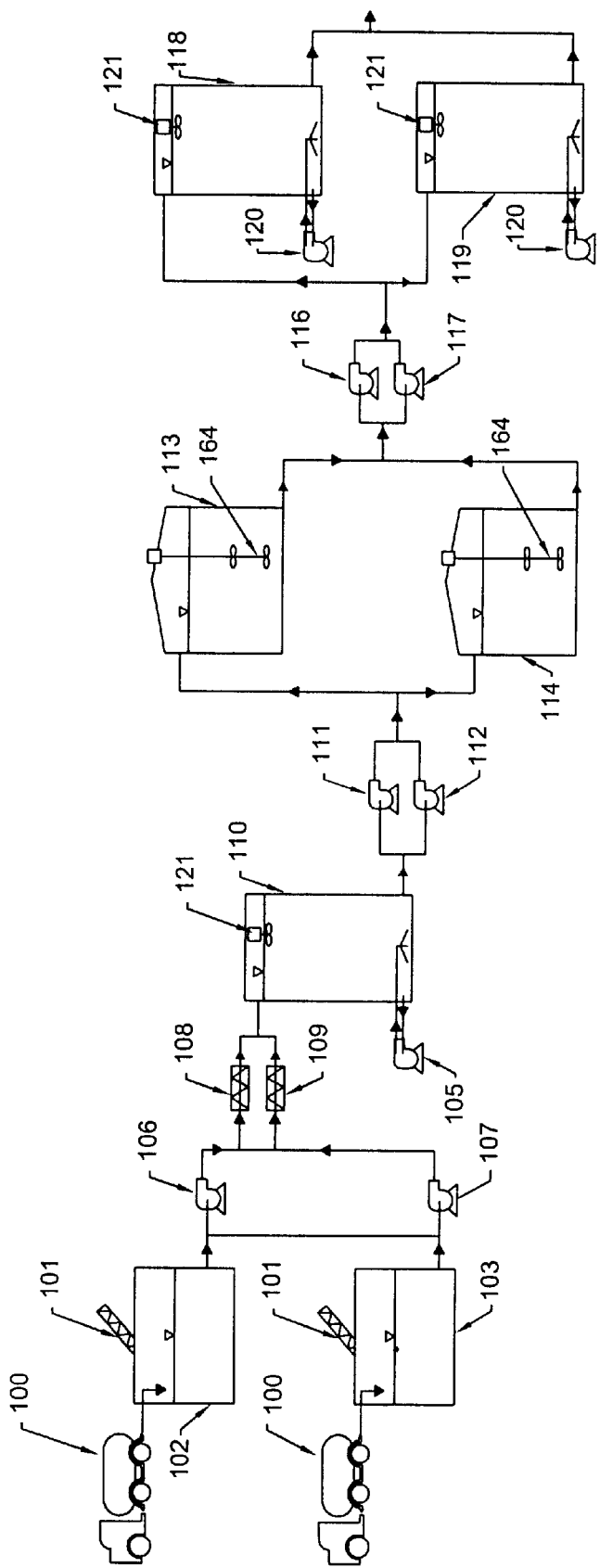
FIGS. 1A, 1B and 1C illustrate a flow diagram of the inventive process.
Figure 1B:
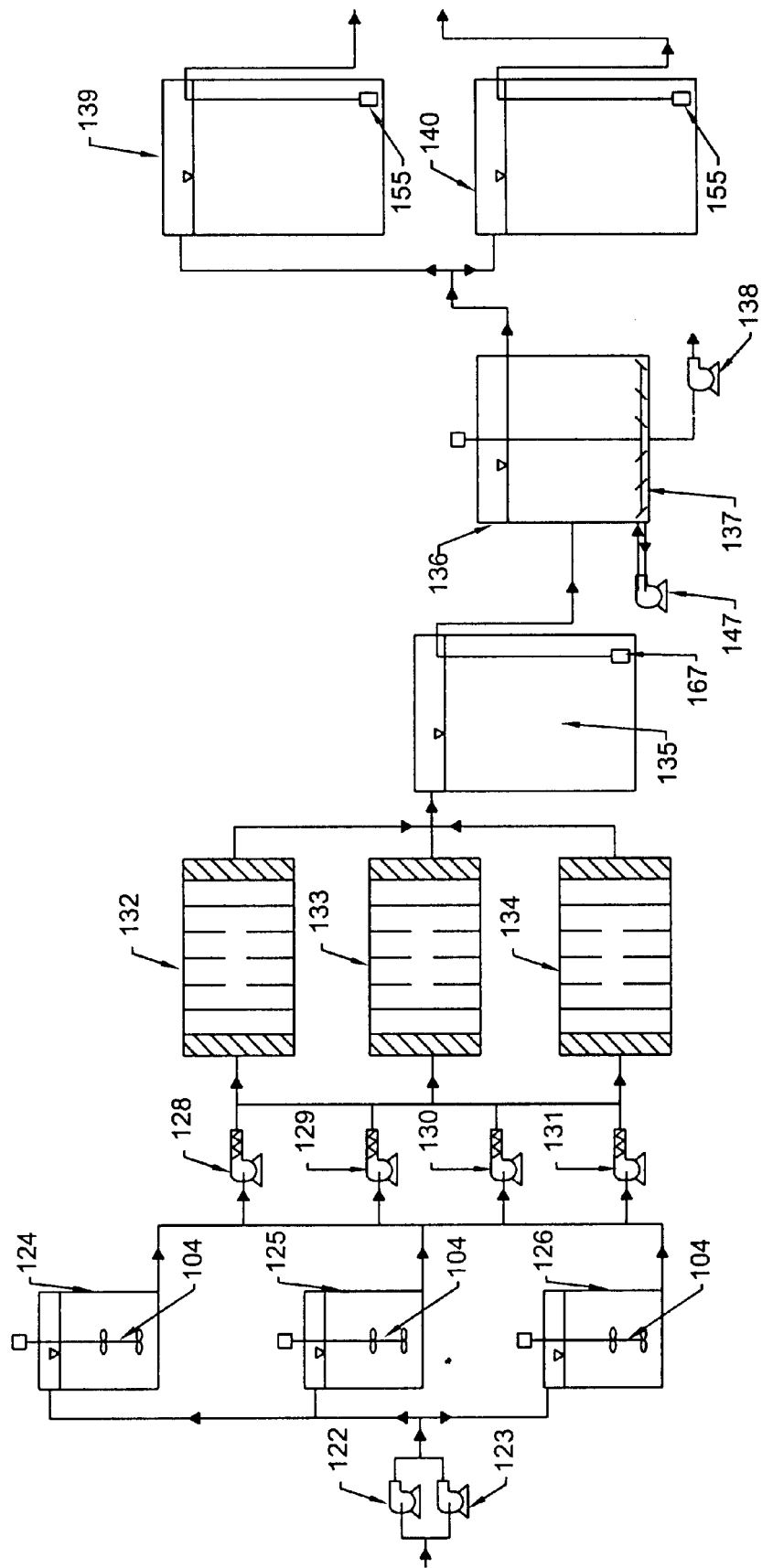
Figure 1C:
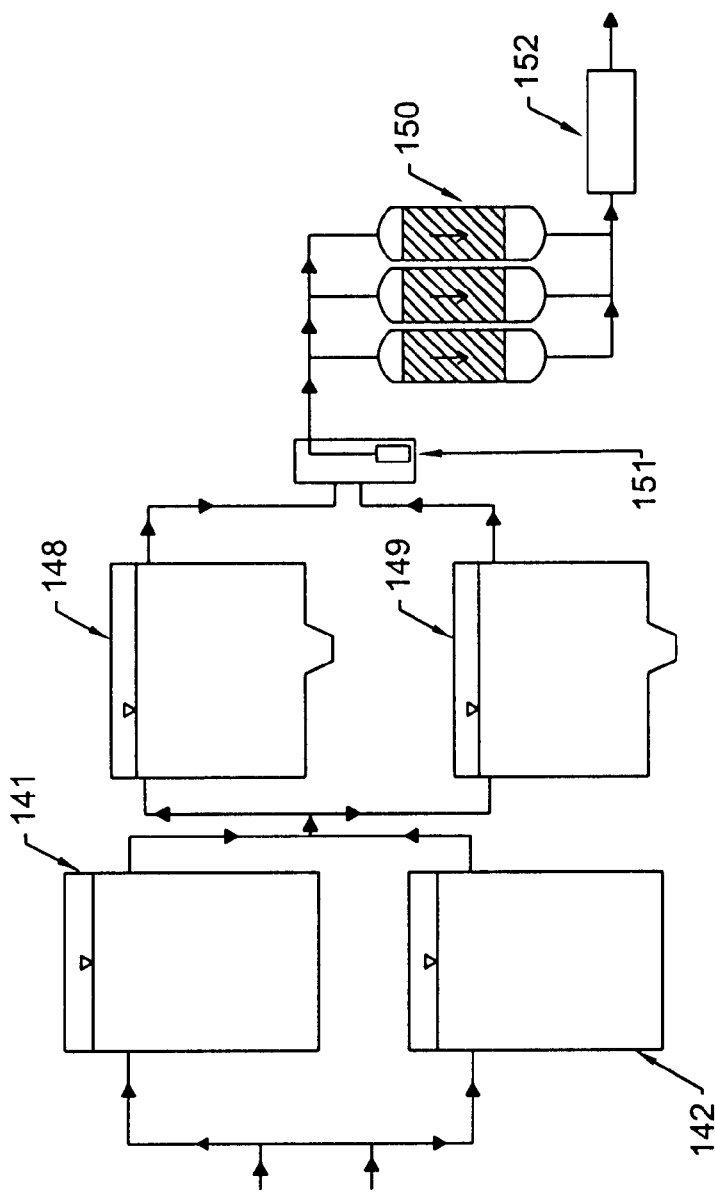

Turning now in detail to FIGS. 1A, 1B and 1C, an illustrative embodiment of the invention will be described. According to the inventive method, grease trap waste and other forms of septage are retrieved from their respective holding tanks by a septage pump truck 100. As shown in FIG. 1A, the collected waste is transferred into the treatment facility from the septage pump truck 100 into a first septage screening box 102 or a second septage screening box 103.

The septage screening boxes 102, 103 are designed to accommodate the simultaneous discharge of multiple septage pump trucks 100 discharging at approximately a maximum combined rate of 1000 gallons per minute of septage containing up to 5 percent solids.

The septage screening boxes 102, 103 consist of a stainless steel tank, motor operated inlet valves, bar screen with self cleaning rotating rake, spray wash system and a control panel for manual or automatic operation.

The screening boxes' 102, 103 bar screens have one-quarter inch bar spacing. This bar spacing allows the removal of debris such as hair, plastics, utensils, rocks and hygienic materials. The debris collected in the bar screen is removed from the screening area by a rotating rake that passes through the full length of the bars. The rotating rake drops the collected screenings into a central screw conveyor hopper. A screw conveyor transports the screenings to a discharge chute. During transport the screenings are compacted and dewatered.

The screenings are spray washed in two separate stages along the screw conveyor to return organic materials to the liquid stream. The treatment process, according to the invention, is designed to treat a large percentage of grease. The spray wash system is therefore supplied with hot water in order to liquefy incoming grease. The spray wash system discharges approximately 5 to 15 gallons per minute ("gpm"). The treatment process utilizes approximately 2,000 gallons per day of spray wash water that is added to the process flow.

After debris removal by septage screening boxes 102, 103, the septage is pumped via a first transfer pump 106 and a second transfer pump 107 through sludge grinders 108, 109. The transfer pumps 106, 107 have a pumping capacity of approximately one thousand gallons per minute within this illustrative embodiment. The sludge grinders 108, 109 grind oversize materials passing through the septage screening boxes 102, 103 protecting downstream process equipment.

The ground septage then empties into a receiving tank 110. In the illustrative embodiment, the receiving tank 110 has a capacity of approximately 125,000 gallons and serves as a buffer for surges in daily septage receipts form septage haulers. The receiving tank 110 is sized according to the operating requirements and desired capacity of the treatment facility. Additionally, multiple receiving tanks can be incorporated to handle heavy volume treatment facilities. The receiving tank 110 is equipped with a jet mixer 105 that keeps solids suspended within the screened and ground septage while it is held in the receiving tank 110. The receiving tank 110 is further equipped with a floatables re-entrainment device 121 that entrains floatable material within the screened and ground septage.

The septage is transferred from the receiving tank 110 by a third transfer pump 111 and a fourth transfer pump 112. The transfer pumps 111, 112 have a pumping capacity of approximately 700 gpm and transfer septage within the receiving tank 110 into a series of pasteurization tanks. This series of pasteurization tanks within this illustrative embodiment is comprised of a first pasteurization tank 113 and a second pasteurization tank 114. The pasteurization tanks 113, 114, each have a capacity of approximately 13,529 gallons. According to the inventive process, each tank receives approximately 10,150 gallons per batch for treatment.

Figure 2:
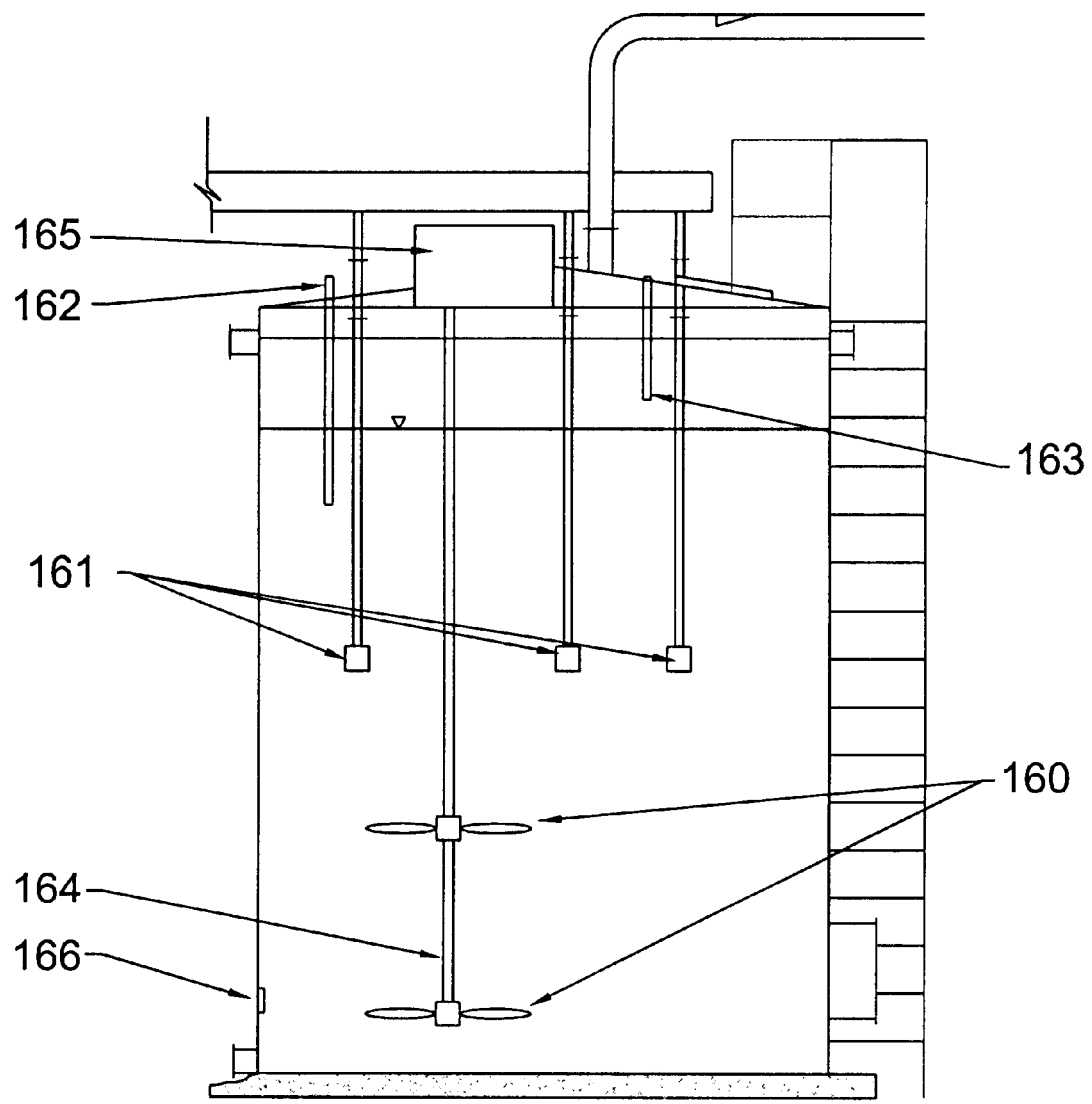
FIG. 2 illustrates a cut-a-way view of the inventive pasteurization tank according to the invention.

As shown in FIG. 2, the pasteurization tanks 113, 114 have agitators 164 mounted within to prevent suspended solids from settling to the bottom of the tanks. Agitators 164 have agitating blades 160 and a motor and drive assembly 165. Each pasteurization tank has three sparge tubes 161 equipped with nozzles to introduce steam directly into the septage and a temperature probe 162, a level probe 163 and a pressure level sensor 166 to control the process. Rapid circulation within the pasteurization tanks 113,114 caused by the sparge tubes 161 and agitators 164 makes certain even temperatures are maintained throughout the thermal mass within the batch. It is contemplated within the scope of this invention that additional pasteurization tanks can achieve an increase in capacity of the treatment facility.

A batch of septage is pumped from the receiving tank 110 into one of the pasteurization tanks 113, 114. Steam, at a temperature of approximately 245° F. and a pressure of approximately 10–15 psig, is injected into the septage through sparge tubes 161 until the temperature of the septage reaches a minimum of 158° F. The septage will be held at this temperature for at least 30 minutes or longer according to Federal and/or State requirements for pathogen reduction.

The pasteurization steam is generated from a boiler that is sized to provide enough heat energy to raise the temperature of a batch, that is approximately 10,150 gallons, of septage and screenings wash water from 40° F. to 158° F. (70° C.) in 60 minutes. A septage batch at 40° F. is about the coldest that is expected to be encountered during the winter months. Average batch ambient temperatures will be much higher than 40° F. and, therefore, less heat energy will be required to raise batch temperatures to 158° F. If batch temperatures are encountered below 40° F., pasteurization heat cycles are extended beyond 60 minutes to compensate.

The number of BTU per hour that the steam boiler must provide to raise the temperature of a batch, 10,150 gallons, of septage and screenings wash water from 40° F. to 158° F. (70° C.) in 60 minutes are as follows:

$$\text{BTU/hr} = 10{,}150 \text{ gal} \div 60 \text{ min} \times 8.3453 \text{ lbs/gal} \times \quad \text{(equation 1)}$$
$$60 \text{ min/hr} \times 118° \text{ F.} = 9{,}995{,}166 \text{ BTU/hr}$$

$$\text{Boiler Horsepower Required} = \quad \text{(equation 2)}$$
$$9{,}995{,}166 \text{ BTU/hr} \div 33{,}479 \text{ BTU/hr/hp} = 299 \text{ hp}$$

The treatment process within this illustrative embodiment will need approximately a 300 hp boiler to meet the heat energy needs for pasteurization. A 300 hp boiler can provide approximately 10,043,000 BTU/hr and has a steam output of approximately 10,350 lb/hr. After injection, the steam releases its heat energy to the septage, cools and condenses. 10,350 lb/hr of steam translates into 20.67 gpm of steam condensate. Approximately 1,240 gallons of steam condensate will be added to each batch of septage and approximately 12,402 gallons per day of steam condensate will be added to the process flow.

The pasteurized septage is pumped via a fifth transfer pump 116 and a sixth transfer pump 117 from the pasteurization tanks 113, 114, to a first cooling tank 118 and a second cooling tank 119. The transfer pumps 116, 117 have the capacity to pump approximately 800 gpm within this illustrative embodiment. The pasteurized septage is cooled within the cooling tanks 118, 119 overnight to ambient temperature. The temperature of the pasteurized septage is lowered within the cooling tanks 118, 119 to ensure that grease which may have liquefied during the pasteurization process will have time to congeal and therefore will not blind off the filter press clothes. Each of the cooling tanks 118, 119 is configured to hold approximately one day's capacity of pasteurized septage and internal process flows which is approximately 135,000 gallons in this illustrative embodiment. The cooling tanks 118, 119 each have a jet mixer 120. The jet mixers 120 prevent suspended solids within the pasteurized septage from settling to the bottom of the cooling tanks 118, 119. The cooling tanks 118, 119 also are equipped with floatable re-entrainment devices 121 to entrain floatable material within the waste stream.

The cooling tanks 118, 119 receive additional process waste materials that are produced downstream within the inventive process. Downstream process waste consisting of clarifier sludge, clarifier scum and sand filter backwash are incorporated into the pasteurized septage.

The cooled pasteurized septage along with downstream waste are pumped via a seventh transfer pump 122 and an eight transfer pump 123 to a first filter press feed tank 124, a second filter press feed tank 125 and a third filter feed tank 126. The transfer pumps 122, 123 have the capacity to pump approximately 670 gpm within this illustrative embodiment. The filter press feed tanks 124, 125, 126 are equipped with agitators 104 to facilitate mixing of the components within the filter feed tanks 124, 125, 126. Hydrated lime is added to the mixture within the filter press feed tanks 124, 125, 126. The hydrated lime is mixed with the pasteurized septage and downstream waste to aid in dewatering and filter cake formation in the filter presses and to raise the pH of the filter cake to reduce vector attraction.

Because dilute slurries are easily pumped, a lime slurry is created to facilitate lime introduction into the filter press feed tanks 124, 125, 126. Hydrated lime contained in a lime silo is mixed with water in a lime slurry tank housed in the base of the lime silo (not shown). Water is added at the rate of I gallon of water per pound of hydrated lime creating a 12% solution. It is contemplated within the scope of this invention that other alkaline compounds that are able to provide filter cake formation and the necessary pH desired that are known within the art may be used.

The pasteurized septage and downstream waste from the cooling tanks 118,119 and hydrated lime from the lime slurry tank are pumped into filter press feed tanks 124, 125, 126 where they are mixed together by the agitators 104. Additionally, calcium carbonate precipitate collected from the downstream neutralization/precipitation process is also added to filter press feed tanks 124, 125, 126. Hydrated lime is added to the pasteurized septage at a rate of up to 40% of the dry solids weight of the pasteurized septage and downstream waste. The addition of the hydrated lime causes the pH of the mixture to rise to at least 12. The controlling factors determining the amount of lime addition are the formation of a high solids content filter cake in the filter presses and the resulting pH of the filter cake. Sufficient lime is added to ensure the formation of a high solids content filter cake and that the pH of the filter cake will maintain, without the addition of more alkali, at least 12 for two hours and at least 11.5 for an additional 22 hours. The preceding parameters for filter cake pH and time are in accordance with regulatory requirements.

Filter press feed tanks 124, 125, 126 are sized to hold a batch of approximately 10,000 gallons of cooling tank contents and lime slurry and have adequate free board, 2 feet. The filter press feed tanks 124, 125, 126 in this illustrative embodiment each have a total capacity of approximately 11,838 gallons. The agitators 104 within the filter press feed tanks 124, 125, 126 prevent suspended solids from settling to the bottom of the tanks and ensure adequate and consistent septage-lime mixing. Each filter press feed tank 124, 125, 126 also has a pH probe, level probe and level sensor to control the process. Cooling tank contents, lime slurry and calcium carbonate precipitate are pumped into the filter press feed tanks 124, 125, 126 and mixed for approximately 45 minutes prior to being fed into a filter press.

The septage, lime slurry and calcium carbonate precipitate mixture is fed into filter presses via a first air diaphragm pump 128, a second air diaphragm pump 129, a third air diaphragm pump 130 and a fourth air diaphragm pump 131. Other types of pumps known within the art may be used. These diaphragm pumps 128, 129, 130, 131 have a capacity of approximately 500 gpm and transfer the lime septage mixture into a first filter press 132, a second filter press 133, and a third filter press 134. The lime septage mixture contains an elevated pH causing the filter cake (sludge) dropped from the filter presses to have a reduced potential to attract vectors (rodents, birds, insects, and other organisms that can transport pathogens).

The filter presses 132, 133, 134 are low pressure (100 psig) filter presses that separate the solid and liquid fractions of the waste stream. The filter presses 132, 133, 134 have polypropylene recessed chamber plates with center feed and discharge through corner ports and have core blow down devices and plate shifters. Opening and closing of the plates is automatic and electro-hydraulically controlled. The filter presses 132, 133, 134 produce a filter cake with a solids content of approximately 40 to 50 percent. Other filter presses that are known within the art may be used.

Liquid passing through the filter presses will have a pH of at least 12 and be saturated with calcium from the lime addition. The pH of the filter liquid must be lowered and the majority of the calcium must be removed prior to introduction into downstream biological processes.

The liquid recovered form the filter presses is transferred to a first equalization tank 135 where it is held prior to transfer via a submersible pump 167 to a neutralization precipitation tank 136. The first equalization tank 135 prevents surges of filter press liquid from affecting the downstream treatment process. The pH of the pressed liquid will be reduced to approximately 8 in the neutralization precipitation tank 136 by the injection of carbon dioxide $CO_2$. When $CO_2$ is dissolved in the recovered filter press liquid three species are formed: carbonic acid, bicarbonate and carbonate. Free hydrogen ions are produced which react with the hydroxides lowering the pH. The amount of carbon dioxide needed to lower the pH of the recovered filter press liquid is based on phenolphthalein (P) and methyl orange (M) alkalinity. Carbon dioxide requirements will be approximately 17 lbs of $CO_2$ per 1000 gallons of filtrate to be neutralized. As the pH of the liquid is lowered, insoluble calcium carbonate is formed and precipitates out of solution.

The calcium carbonate precipitate falls to the bottom of the neutralization precipitation tank 136 where a scrapper 137 aids in the gathering of the precipitate for transfer via a precipitation pump 138 upstream to the filter press feed tanks 123, 124 for removal from the liquid stream in the filter presses 132, 133, 134.

Neutralized filter press liquid flows into a first equalization tank 139 and a second equalization tank 140. The equalization tanks 139, 140 allow for retention of the neutralized filter press liquid and balancing of downstream treatment processes with upstream treatment processes. As the treatment processes upstream of equalization tanks 139, 140 operate during a 12-hour workday and the biological and other downstream processes are designed to treat the same volume of liquid over a 24-hour period, a minimum of 12 hours retention time must be provided. Equalization tanks 139, 140 provide 88,000 gallons or approximately 16 hours of retention time.

Figure 3:
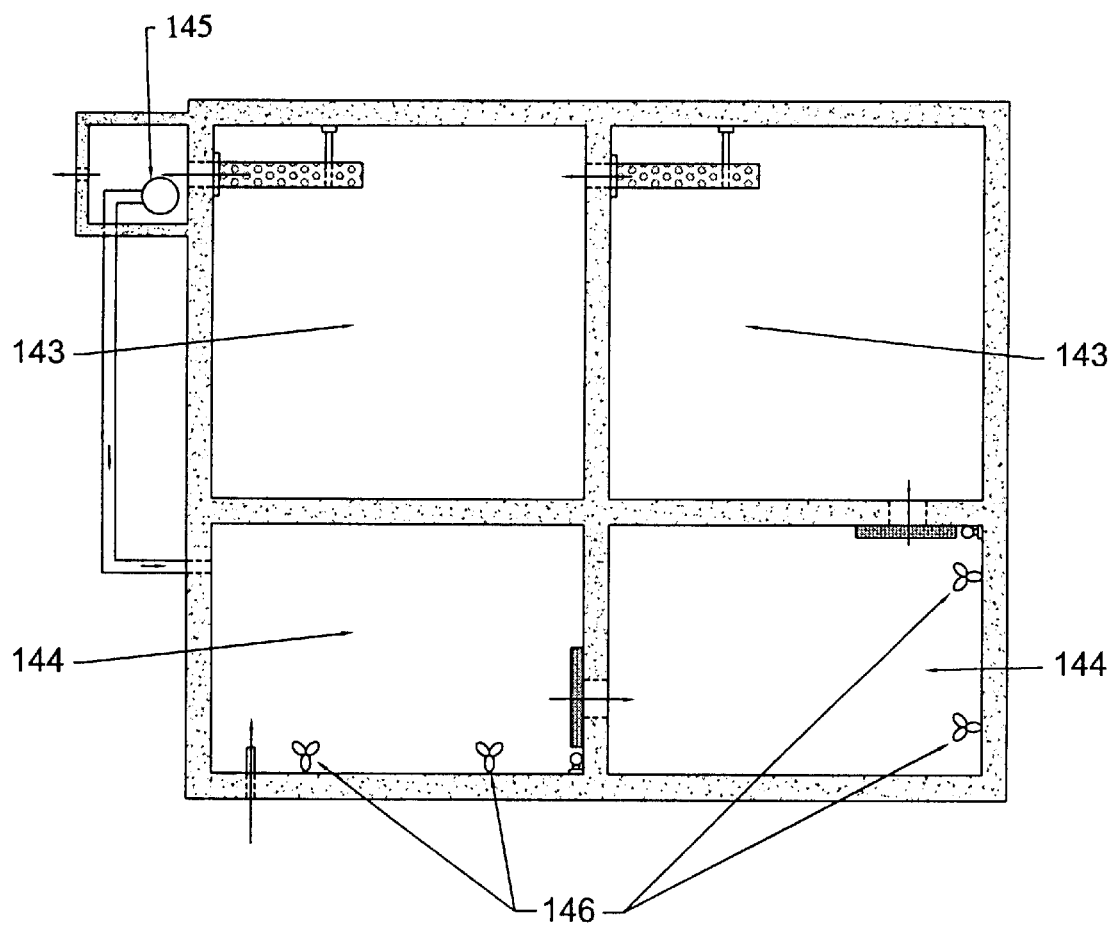
FIG. 3 illustrates the various components within the biological treatment reactor according to the invention.

The retained liquid within the equalization tanks 139, 140 is pumped via submersible pumps 155 to a first biological treatment reactor 141 and a second biological treatment reactor 142. Each biological treatment reactor 141, 142 is comprised of two aerobic tanks 143 and two anaerobic tanks 144 as shown in FIG. 3. Fixed film (Attached Growth) biological processes are used to achieve BOD reduction, nitrification and denitrification. Suspended Growth or other biological treatment processes known in the art may be employed. The biological treatment processes according to the invention employ carrier elements that move along with the water in the biological treatment reactors 141, 142 to support the growth of microbial populations. The biofilm carrier elements are made of high-density polyethylene, have high biofilm surface area and a specific gravity of approximately 0.96. Stainless steel screens keep the biofilm carrier elements within the biological treatment reactor 141, 142. The biological treatment reactors 141, 142 operate continuously, are non-clogging, need no backwashing, and have low head loss. Circulation within biological treatment reactors 141, 142 is produced by coarse-bubble aeration systems in aeration zones 143 and mechanical mixers 146 in anaerobic zones 144.

The anaerobic tanks 144 have a 43.9% volumetric filling of carrier elements and the aerobic tanks 143 have a 49.8% volumetric filling. The tanks can be filled to 65% without a noticeable decrease in treatment performance. The anaerobic tanks 144 can be configured to denitrify up to 48% more nitrates and the aerobic tanks 143 can be configured to remove up to 30% more BOD or nitrify up to 30% more nitrogen. This increase in treatment capacity is achieved by adding additional carrier elements to each tank, up to 65% of the tank's volume, and increasing the airflow to each of the aerobic tanks 143 to compensate for the increase in organic and ammonia loads.

BOD reduction is performed primarily in the first of the two aerobic tanks 143. Carbon oxidizing bacteria consume and remove biodegradable matter, carbon, reducing the level of soluble BOD in the incoming liquid to 15 mg/l or lower. Enhancing and supporting biological activity, the level of dissolved oxygen within the aerobic tanks 143 is maintained at 4.0 mg/l by means of air blowers and an aeration grid at the bottom of the tanks. The aeration grid also ensures good circulation of the wastewater and carrier elements within the aerobic tanks 143.

At soluble BOD concentrations of 15 mg/l or less in the second aerobic tank 143, nitrification takes place. Ammonia-oxidizing bacteria are predominant and convert ammonia-nitrogen to nitrate-nitrogen. As nitrification is an aerobic process, the level of dissolved oxygen in the tank 143 is also maintained at 4.0 mg/l by means of air blowers and an aeration grid. And as in the first aerobic tank 143, the aeration grid also ensures good circulation of the wastewater and carrier elements within the tank.

The nitrification process reduces alkalinity when converting ammonia to nitrate and if the wastewater does not have enough alkalinity available for the nitrification of the ammonia pH would start to decrease. The process liquid at this stage has sufficient alkalinity in the form of calcium bicarbonate and sufficient pH, 8, to offset the reduction in alkalinity.

Denitrification occurs in the anaerobic tanks 144. Bacteria reduce nitrate- and nitrite-nitrogen to nitrogen gas. To optimize the process, the pH must be controlled in the range of 7.0 to 7.6, sufficient biologically degradable organic material to sustain bacterial growth must be provided, and the environment must be without free oxygen.

After measuring and allowing for pH reduction within the nitrification process, pH in the anaerobic tanks 144 is maintained within the desired range by regulating the pH of the liquid exiting the neutralization precipitation tanks.

Sufficient biologically degradable organic material to sustain bacterial growth is contained in the liquid arriving from the equalization tanks 139, 140. Liquid arriving from the equalization tanks 139, 140 enters the biological treatment process through the anaerobic tanks 144. Therefore, bacteria in the anaerobic tanks 144 have access to biologically degradable material before it is removed in the aerobic tanks 143. No air is supplied to the anaerobic tanks 144. Mixers are provided within the anaerobic tanks 144 to ensure good circulation of the wastewater and carrier elements within the tanks.

Turning to FIG. 3, wastewater is recycled within the biological treatment reactors 141, 142 from the second aerobic tank 143, nitrification tank, to the anaerobic tanks 144, denitrification tanks, by means of submersible pumps 145. The amount of recycled wastewater is determined by the amount of nitrite- and nitrate-nitrogen requiring denitrification which fluctuates with a number of factors such as; effluent criteria, the amount of ammonia-nitrogen introduced into the biological treatment process, the amount of ammonia-nitrogen consumed in BOD reduction and the amount of ammonia-nitrogen which has been nitrified. Through the use of the submersible pumps and regulating flow valves, the amount of recycle can quickly and easily be regulated to meet fluctuations within the biological treatment process.

The waste stream exiting the biological treatment process contains undesirable components produced by the biological treatment processes which are removed by clarifying the waste stream. Sludge and scum from the biological treatment processes are collected and removed from the liquid waste stream in a first clarifier 148 and a second clarifier 149. Removed sludge and scum is pumped back to the cooling tanks 118, 119 for ultimate removal in the filter presses 132, 133, 134.

The clarifiers 148, 149 are circular with a rotating arm skimmer, scum box, rotating sludge collector, and sloped bottom. The clarifiers 148, 149 are capable of adjustable, timed sludge and scum pumping.

The clarified liquid waste stream is pumped via a submersible pump 151 through a sand filter system 150. The submersible pump 151 has a pumping capacity of approximately 90 gpm. The sand filter system 150 is a fully automatic, skid mounted, three-cell pressure system. Using filtered wastewater from the other two cells, the sand filter system 150 backwashes each of the three media beds sequentially. The system allows wastewater filtration to continue during backwash cycles. The system has approximately 14.7 ft$^2$ of filter media area. The sand filter back wash is pumped to the cooling tanks 118, 119 for ultimate removal in the filter presses 132, 133, 134. It is contemplated within the scope of this invention that other methods known in the art, such as membrane filtration, may be used.

The sand filtered waste stream is than treated by an UV disinfection system 152 to kill live biological organisms from the aerobic 143 and anaerobic 144 treatment processes which pass through the clarifiers 148, 149 and sand filter system 150. UV disinfection aids in the control of injection well fouling due to bacterial clogging. The UV disinfected water is used within the inventive process for lime slurry water, boiler makeup water and septage screenings wash water. Other methods of disinfection known within the art, such as chlorination, may be used. The remaining water in excess of internal process requirements is discharged to the environment. The inventive process embodies the use of injection wells to return the processed water to the environment. However, other methods known in the art, such as discharge to open sand beds, surface waters or sewer systems, may be used.

While the invention has been described in connection with a specific illustrative embodiment thereof, it will be understood that it is capable of further modifications and this application is intended to cover any variations, uses, or alterations of the invention. In general, the principles of the invention and including such departures from the present disclosure as come within known or customary practice within the art to which the invention pertains and as may be applied to the essential features hereinbefore set forth and as follows in the scope of the appended claims.

Various other changes, omissions and additions in the form and detail of the present invention may be made therein without departing from the spirit and scope of the invention. Therefore, the above description should not be construed as limiting, but merely as exemplification of the various embodiments.

What is claimed is:

1. A method for treating septage to produce a beneficial biosolid and dischargeable water from said septage comprising the following steps:

providing septage having a liquid component and a solid component;

screening said septage to remove large, inorganic debris and further grinding said septage to reduce the size of any remaining debris;

pasteurizing said septage, wherein said pasteurization substantially reduces pathogens within said septage;

adding an alkaline compound to said pasteurized septage wherein said alkaline compound aids in dewatering of said septage and elevates the pH of said septage thereby reducing the attraction of said septage to vectors;

pressing said alkaline conditioned septage in a filter press producing a filter cake, biosolid, and filter press filtrate, wherein said bio-solid is removed from said treatment process;

injecting carbon dioxide into said filter press filtrate, wherein said injection of carbon dioxide lowers said pH of said filter press filtrate thereby precipitating out calcium present within said filter press filtrate causing the resulting filtrate to be substantially calcium free;

treating said calcium free filtrate with a biological treatment processes;

clarifying said treated filtrate to remove debris from said biological treatment processes;

filtering said clarified liquid; and disinfecting said filtered liquid and thereby producing said dischargeable water.

2. The method of claim 1 wherein said pasteurization is achieved by injecting steam into said septage.

3. The method of claim 1 wherein said pasteurization is achieved by heating with fossil fuels.

4. The method of claim 1 wherein said pasteurization is achieved by heating with electrical elements.

5. The method of claim 1 wherein said bio-solids are sludge acceptable for land application for beneficial purposes under Federal and State regulations.

6. The method of claim 1 wherein said alkaline compound is hydrated lime.

7. The method of claim 1 wherein said alkaline compound raises the pH of said filter cake to at least 12 thereby reducing vector attraction.

8. The method of claim 1 wherein injection of said carbon dioxide lowers the pH of said filter press filtrate to at least 8 by forming carbonic acid, bicarbonate and carbonate.

9. The method of claim 1 wherein said alkaline addition will be 30–40 percent of the dry solids weight of said septage.

10. The method of claim 1 wherein said biological treatment is a fixed film biological process that achieves BOD reduction, nitrification and denitrification.

11. The method of claim 1 wherein said biological treatment is a suspended growth process.

12. The method of claim 1 wherein said filtration is a sand filter.

13. The method of claim 1 wherein said filtration is a membrane filter.

14. The method of claim 1 wherein said disinfection is by ultra violet light.

15. The method of claim 1 wherein said disinfection is by chlorination.

16. The method of claim 1 wherein said discharge water meets Federal and State drinking water standards.

17. An apparatus for treatment of septage comprising:

a septage screening box for receiving said septage, said septage screening box having a grid to remove large inorganic debris, a septage grinder that receives said septage from said septage screening box whereby said septage grinder reduces the size of solids remaining in said screened septage allowing said septage to move more easily through said apparatus;

a pasteurization tank that receives ground septage from said septage grinder, wherein said ground septage is heated to a level to achieve pathogen reduction;

a filter press feed tank that receives pasteurized septage, wherein an alkaline compound is added to said pasteurized septage to reduce vector attraction and aid in the dewatering of said pasteurized septage;

a filter press that receives said alkaline conditioned septage and removes a liquid component of said alkaline conditioned septage and produces a beneficial biosolid;

a neutralization tank that receives said liquid component and lowers its pH:

a biological treatment reactor that receives said liquid component, said biological treatment reactor having aerobic treatment tanks and anaerobic treatment tanks;

a clarifier that receives biologically treated liquid component, wherein said clarifier removes debris produced by said biological treatment reactor;

a filter system that receives the clarified liquid component; and a disinfection system that receives the filtered liquid component and kills any remaining biological organisms.

18. The apparatus of claim 17 wherein said pasteurization tank has a series of sparge tubes for injecting steam into said septage and a series of mixers allowing for the even distribution of said steam.

19. The apparatus of claim 17 wherein said pasteurization tank has thermal exchange tubes throughout and said thermal exchange tubes are heated by fossil fuels.

20. The apparatus of claim 17 wherein said pasteurization tank is heated by a series of electrical thermal elements.

21. The apparatus of claim 17 wherein said alkaline compound is hydrated lime.

22. The apparatus of claim 17 wherein said alkaline compound raises the pH of a filter cake, produced by said filter press, to at least 12 thereby reducing vector attraction.

23. The apparatus of claim 17 wherein said neutralization tank receives carbon dioxide thus lowering the pH of the filter press liquid component to at least 8 by forming carbonic acid, bicarbonate and carbonate.

24. The apparatus of claim 17 wherein said biological treatment reactor is configured to provide a fixed film biological process that achieves BOD reduction, nitrification and denitrification.

25. The apparatus of claim 17 wherein said biological treatment reactor is configured to provide a suspended growth biological process that achieves BOD reduction, nitrification and denitrification.

26. The apparatus of claim 17 said filtration system is a sand filter.

27. The apparatus of claim 17 wherein said filtration system is a membrane filter.

28. The apparatus of claim 17 wherein said disinfection system uses of ultra violet light.

29. The apparatus of claim 17 wherein said disinfection system uses chlorination.

\* \* \* \* \*